United States Patent
Woo et al.

(10) Patent No.: US 8,771,761 B2
(45) Date of Patent: *Jul. 8, 2014

(54) **COMPOSITION FOR TREATING ATOPIC DERMATITIS COMPRISING EXTRACTS OF BAMBOO AND *SCUTELLARIA***

(75) Inventors: Sung Sick Woo, Seoul (KR); Dong Seon Kim, Daejeon (KR); Young Chul Lee, Daejeon (KR); Eun Jung Son, Chungcheongnam-do (KR)

(73) Assignee: Unigen, Inc., Cheonan-si (KR)

( * ) Notice: Subject to any disclaimer, the term of this patent is extended or adjusted under 35 U.S.C. 154(b) by 0 days.

This patent is subject to a terminal disclaimer.

(21) Appl. No.: 13/586,741

(22) Filed: Aug. 15, 2012

(65) Prior Publication Data

US 2013/0064910 A1    Mar. 14, 2013

Related U.S. Application Data

(63) Continuation of application No. 12/445,159, filed as application No. PCT/KR2007/005004 on Oct. 12, 2007, now Pat. No. 8,247,007.

(30) Foreign Application Priority Data

Oct. 12, 2006   (KR) .......................... 10-2006-0099182

(51) Int. Cl.
*A61K 36/00* (2006.01)
*A61K 36/539* (2006.01)
*A61K 36/899* (2006.01)

(52) U.S. Cl.
USPC ............................ 424/725; 424/741; 424/750

(58) Field of Classification Search
None
See application file for complete search history.

(56) References Cited

U.S. PATENT DOCUMENTS

| | | | |
|---|---|---|---|
| 4,201,776 A | 5/1980 | Naito et al. | |
| 5,098,709 A | 3/1992 | Kang | |
| 5,643,598 A | 7/1997 | Meybeck | |
| 5,650,432 A | 7/1997 | Walker et al. | |
| 5,858,371 A | 1/1999 | Singh et al. | |
| 6,083,921 A | 7/2000 | Xu | |
| 6,555,573 B2 | 4/2003 | Rosenbloom | |
| 7,192,611 B2 | 3/2007 | Jia et al. | |
| 7,514,469 B2 | 4/2009 | Jia | |
| 7,674,830 B2 | 3/2010 | Jia | |
| 7,897,182 B2 | 3/2011 | Woo et al. | |
| 7,972,632 B2 | 7/2011 | Jia | |
| 8,247,007 B2 * | 8/2012 | Woo et al. ...................... 424/741 |
| 2002/0136784 A1 | 9/2002 | Obukowicz et al. | |
| 2002/0146467 A1 | 10/2002 | Jung et al. | |
| 2003/0105030 A1 | 6/2003 | Liao et al. | |
| 2003/0125264 A1 | 7/2003 | Malik | |
| 2003/0166583 A1 | 9/2003 | Yoa-Pu Hu et al. | |
| 2003/0170186 A1 | 9/2003 | Geers et al. | |
| 2003/0203857 A1 | 10/2003 | Ohnogi et al. | |
| 2004/0185124 A1 | 9/2004 | Hayashi | |
| 2004/0220119 A1 | 11/2004 | Jia | |
| 2007/0065524 A1 | 3/2007 | Wang | |
| 2008/0107759 A1 | 5/2008 | Woo et al. | |
| 2008/0214658 A1 | 9/2008 | Woo et al. | |
| 2008/0279969 A1 | 11/2008 | Jo et al. | |
| 2009/0304830 A1 | 12/2009 | Jo et al. | |
| 2011/0117224 A1 | 5/2011 | Woo et al. | |
| 2011/0207806 A1 | 8/2011 | Jia | |

FOREIGN PATENT DOCUMENTS

| | | |
|---|---|---|
| CA | 2 126 513 A1 | 1/1995 |
| CA | 2 451 844 A1 | 1/2003 |
| CA | 2 484 192 A1 | 11/2003 |
| CN | 1057196 A | 12/1991 |
| CN | 1096680 A | 12/1994 |
| CN | 1101856 A | 4/1995 |
| CN | 1177492 A | 4/1998 |
| CN | 1228968 A | 9/1999 |
| CN | 1265895 A | 9/2000 |
| CN | 1285202 A | 2/2001 |
| CN | 1686187 A | 10/2005 |
| EP | 0 296 625 A2 | 12/1988 |
| EP | 0 633 022 B1 | 2/1997 |
| FR | 2 651 132 A1 | 3/1991 |
| FR | 2 687 572 A1 | 8/1993 |
| JP | 57038721 A | 3/1982 |
| JP | 61-50921 A | 3/1986 |
| JP | 61-83179 A | 4/1986 |
| JP | 61-161219 A | 7/1986 |

(Continued)

OTHER PUBLICATIONS

Afolayan et al., "The antimicrobial activity 3,5,7-trihydroxyflavone isolated from the shoots of *Helichrysum aureonitens*," *Journal of Ethnopharmacology* 57(3):177-181, 1997.

(Continued)

*Primary Examiner* — Terry A McKelvey
*Assistant Examiner* — Randall Winston
(74) *Attorney, Agent, or Firm* — Seed IP Law Group PLLC

(57) ABSTRACT

The present invention relates to a composition comprising of plant extract as an active component, specifically, Bamboo extract and *Scutellaria* extract, for the treatment and prevention of atopic dermatitis. The present invention is a natural ingredient obtained from a plant. The present invention can control immune responses by inhibiting the release of histamine and leukotriene, and thus, has effect in the treatment or prevention of allergic diseases, inflammatory diseases and skin diseases, specifically atopic dermatitis. The present invention has been proven safe and beneficial effecting the treatment of atopic dermatitis through clinical trials, and thus, can be used for the treatment and prevention of atopic dermatitis.

13 Claims, 2 Drawing Sheets

(56) References Cited

FOREIGN PATENT DOCUMENTS

| | | | |
|---|---|---|---|
| JP | 61-233627 A | 10/1986 |
| JP | 63-27435 A | 2/1988 |
| JP | 07223941 A | 3/1991 |
| JP | 3-240725 A | 10/1991 |
| JP | 403251518 A | 11/1991 |
| JP | 5-271088 A | 10/1993 |
| JP | 7-25761 A | 1/1995 |
| JP | 407017847 A | 1/1995 |
| JP | 7-55895 B2 | 6/1995 |
| JP | 7-252158 A | 10/1995 |
| JP | 7-277942 A | 10/1995 |
| JP | 8-26969 A | 1/1996 |
| JP | 08026969 A * | 1/1996 |
| JP | 8-104628 A | 4/1996 |
| JP | 09278662 A | 10/1997 |
| JP | 10-182415 A | 7/1998 |
| JP | 10-287528 A | 10/1998 |
| JP | 2000/044481 A | 2/2000 |
| JP | 2000-506901 A | 6/2000 |
| JP | 2000-31954 A | 11/2000 |
| JP | 2003-212786 A | 7/2003 |
| JP | 2003212786 A * | 7/2003 |
| KR | 1996-0003725 A | 2/1996 |
| KR | 1996-0040370 A | 12/1996 |
| KR | 2001-0017481 A | 3/2001 |
| KR | 2001-0069130 A | 7/2001 |
| KR | 2002-0013675 A | 2/2002 |
| KR | 2002-0031608 A | 5/2002 |
| KR | 2003-0021640 A | 3/2003 |
| KR | 10-0465113 B1 | 12/2004 |
| KR | 10-0522579 B1 | 10/2005 |
| TW | 2359922 A | 12/1994 |
| WO | 98/49256 A1 | 11/1998 |
| WO | 00/59523 A1 | 10/2000 |
| WO | 00/67749 A1 | 11/2000 |
| WO | 01/30341 A1 | 5/2001 |
| WO | 02/07745 A1 | 1/2002 |
| WO | 02/39973 A2 | 5/2002 |
| WO | 02/47615 A2 | 6/2002 |
| WO | 03/015766 A1 | 2/2003 |
| WO | 03/024470 A1 | 3/2003 |
| WO | 03/092599 A2 | 11/2003 |
| WO | 2004/089392 A1 | 10/2004 |

OTHER PUBLICATIONS

Butenko et al., "Anti-inflammatory properties and inhibition of leukotriene C4 biosynthesis in vitro by flavonoid baicalein from *Scutellaria baicalensis* georgy roots," *Agents Actions Special Conference Issue* 39:C49-051, 1993.
Chen et al., "Oroxylin A inhibition of Lipopolysaccharide-Induced iNOS and COX-2 Gene Expression via Suppression of Nuclear factor-κB activation," *Biochemical Pharmacology* 59(11):1445-1457, Jun. 1, 2000.
Chen et al., "Wogonin, baicalin, and baicalein inhibition of inducible nitric oxide synthase and cyclooxygenase-2 gene expressions induced by nitric oxide synthase inhibitors and lipopolysaccharide," *Biochemical Pharmacology* 61(11):1417-1427, Jun. 1, 2001.
Chi et al., "Effect of wogonin, a plant flavone from *Scutellaria radix*, on the suppression of cyclooxygenase-2 and the induction of inducible nitric oxide synthase in lipopolysaccharide-treated RAW 264.7 cells," *Biochemical Pharmacology* 61:1195-1203, May 15, 2001.
Chung et al., "Pharmacological Effects of Methanolic Extract from the Root of *Scutellaria baicalensis* and its Flavonoids on Human Gingival Fibroblast," *Planta Medica* 61(2):150-153, Apr. 1995.
Colby, "Calculating Synergistic and Antagonistic Responses of Herbicide Combinations," *Weeds* 15(1):20-22, 1967.
Database TCM, "Xiaoer Qingfei Huatan Paoteng Keli and its preparation method/A new Chinese medicine preparation used for the treatment of infantile lung heat and common cold," Oct. 26, 2005, 1 page.

Database WPI, Accession No. 2000-673139, "Specific medicine for treating common cold is made of the Chinese medicinal materials including bupleurum root, white peony root, scutellaria root, pinellia tuber, licorice, ginseng, fresh ginger, lonicera flower, forsythia fruit," Sep. 13, 2000, 6 pages.
Database WPI, Accession No. 2003-355289, "Medicine for preventing and treating eye diseases comprises e.g., chrysanthemum flower, dandelion, forsythia fruit, lonicera flower, scutellaria root, gentian root, andropogon nardus, mulberry root bark and mint or bamboo leaf," Apr. 1, 1998, 1 page.
de la Puerta et al., "Inhibition of Leukocyte Eicosanoid Generation and Radical Scavenging Activity by Gnaphalin, a Lipophilic Flavonol Isolated from *Helichrysum picardii*," *Planta Medica* 65(6):507-511, Aug. 1999.
Friedman et al., "NSAIDs in Dermatologic Therapy: Review and Preview," *Journal of Cutaneous Medicine and Surgery* 6(5):449-459, 2002.
Hu et al., "Evaluation of Antioxidant and Prooxidant Activities of Bamboo *Phyllostachys nigra* Var. *Henonis* Leaf Extract in Vitro," *Journal of Agricultural and Food Chemistry* 48:3170-3176, 2000.
Kawasaki et al., "In Vitro Antiallergic Activity of Flavonoids in Histamine Release Assay Using Rat Basophilic Leukemia (RBL-2H3) Cells," *Journal of the Food Hygienic Society of Japan* 33(5): 497-503, Oct. 1994.
Kikukawa et al., "Mechanisms of suppressive action of TJ114 upon murine type II collagen-induced arthritis," *Ensho* 15(2):129-133, 1995. (Abstract only).
Kim et al., "Pharmacological Activities of Flavonoids (I)—Relationships of Chemical Structure of Flavonoids and their Inhibitory Activity of Hypersensitivities," *Yakhak Hoeji* 34(5): 348-364, 1990. (English Abstract provided.).
Kubo et al., "Studies on *Scutellariae radix*. VII. Anti-arthritic and Anti-inflammatory Actions of Methanolic Extract and Flavonoid Components from *Scutellariae Radix*," *Chemical & Pharmaceutical Bulletin* 32(7):2724-2729, Jul. 1984.
Lee et al., "Antitumor Agents. 49.1 Tricin,Kaempferol-3-0-β-D-Glueopyranoside and (+)-Nortrachelogenin, Antileukemic Principles from *Wikstroemia indica*," *Journal of Natural Products* 44:530-535, Sep.-Oct. 1981.
Nakagami et al., "Anti-complementary substance used as therapeutic agent—comprises gallic acid, methyl gallate, acetyl-salicylic acid, caffeic acid, catechin, epi-gallo-catechin gallate, myricetin, quercitrin and/or baicalein, or their salts," WPI Accession No. 1995-325471 Derwent Abstract XP002418722, & JP 07 223941 A, Aug. 22, 1995, 1 page.
Nakahata et al., "Analysis of Inhibitory Effects of Scutellariae Radix and Baicalein on Prostaglandin $E_2$ Production in Rat C6 Glioma Cells," *The American Journal of Chinese Medicine* 26(3-4):311-323, 1998. (English Abstract included).
Nakahata et al., "Inhibition of mitogen-activated protein kinase cascade by baicalein, a flavonoid of natural origin," *Nippon Yakurigaku Zasshi* 114(Supp. 1):215P-219P, 1999.
Nakajima et al., "Inhibitory Effect of Baicalein, a Flavonoid in Scutellaria Root, on Eotaxin Production by Human Dermal Fibroblasts," *Planta Medica* 67(2):132-135, Mar. 2001.
Otani et al., "Hito-chemical Studies on the Anti-ulcer Effect of Bamboo Grass in Rats," *International Journal of Tissue Reactions* XIII(6):319-332, 1990.
Rasa et al., "Inhibition of inducible nitric oxide synthase and cyclooxygenase-2 expression by flavonoids in macrophage J774A. 1," *Life Sciences* 68(8):921-931, 2001.
Sartor et al., "Inhibition of matrix-proteases by polyphenols: chemical insights for anti-inflammatory and anti-invasion drug design," *Biochemical Pharmacology* 64:229-237, 2002.
Shibata et al., "Pharmacological Study of Kumazasa (Report 1) Acute toxicity, anti-inflammatory and antiulcerative effects of kumazasa water soluble fraction (Folin)," *Folia pharmacol japon* 71(5):481-490, 1975. (English translation provided.), 11 pages.
Tanaka, "Cosmetics for preventing aging of skin, comprises elastase inhibitor such as catechin, flavones, flavonols, flavanone, isoflavanones, coumarin and/or their glycosides" WPI/Thomson Database, Accession No. 2003-451711 [43], Jan. 8, 2003, 4 pages.

(56) References Cited

OTHER PUBLICATIONS

Tsao et al., "Effect of Chinese and Western Antimicrobial Agents on Selected Oral Bacteria," *Journal of Dental Research* 61(9):1103-1106, 1982.

Wilgus et al., "Inhibition of Ultraviolet Light B-Induced Cutaneous Inflammation by a Specific Cyclooxygenase-2 Inhibitor," *Advances in Experimental Medicine and Biology* 507:85-92, 2002.

Wilgus et al., "Topical application of a selective cyclooxygenase inhibitor suppresses UVB mediated cutaneous inflammation," *Prostaglandins & other Lipid Mediators* 62(4):367-384, 2000.

Yamahara et al, "Inhibitory effect of crude Chinese drugs on the denaturation of human γ-globulin induced by heat and copper (2+)," *Shoyakugaku zasshi* 35(2):103-107, 1981. (Abstract only).

Zhang et al., *China Journal of the Chinese Materia Medical* 27(4):254-257, 2002, 5 pages. (English translation provided.).

"Scutellaria Root / *Official Monographs for Part II*," in The Japanese Pharmacopoeia, 14th ed. (English version), Society of Japanese Pharmacopoeia, Tokyo, Japan, 2001, pp. 1042-1043. (4 pages).

Chou et al., "The Antiinflammatory and Analgesic Effects of Baicalin in Carrageenan-Evoked Thermal Hyperalgesia," *Anesth Analg* 97:1724-1729, 2003.

Gafner et al., "Evaluation of the anti-inflammatory properties of skullcap (*Scutellaria lateriflora* L.) extracts in different in vitro models," 2004 International Congress on Natural Products Research, Phoenix, Arizona, Jul. 31-Aug. 4, 2004, P:60 and poster. (3 pages).

Itoigawa et al., "Structure-activity relationship of cardiotonic flavonoids in guinea-pig papillary muscle," *Journal of Ethnopharmacology* 65:267-272, 1999.

Kalkbrenner et al., "In vitro Inhibition and Stimulation of Purified Prostaglandin Endoperoxide Synthase by Flavonoids: Structure-Activity Relationship," *Pharmacology* 44:1-12, 1992.

Kaneko et al., "Protective Effect of Flavonoids on Endothelial Cells against Linoleic Acid Hydroperoxide-induced Toxicity," *Biosci Biotechnol Biochem* 63:323-328, 1999.

Kimura et al., "Effects of Baicalein Isolated from *Scutellaria baicalensis* Radix on Adhesion Molecule Expression Induced by Thrombin and Thrombin Receptor Agonist Peptide in Cultured Human Umbilical Vein Endothelial Cells," *Planta Medica* 67:331-334, 2001.

Krakauer et al., "The flavonoid baicalin inhibits superantigen-induced inflammatory cytokines and chemokines," *FEBS Letters* 500:52-55, 2001.

Kubo et al., "Studies on Scutellariae Radix, Part II: The Antibacterial Substance," *Planta Medica* 43(2):194-201, 1981.

Laughton et al, "Inhibition of Mammalian 5-Lipoxygenase and Cyclo-Oxygenase by Flavonoids and Phenolic Dietary Additives," *Biochemical Pharmacology* 42(9): 1673-1681, 1991.

Lee et al., "Salicylic Acid Peels for the Treatment of Acne Vulgaris in Asian Patients," *Dermatol Surg* 29(12):1196-1199, 2003.

Leyden, "A review of the use of combination therapies for the treatment of acne vulgaris," *J Am Acad Dermatol* 49(3 Suppl):S200-S210, 2003. (Abstract only).

Li et al., "The flavonoid baicalin exhibits anti-inflammatory activity by binding to chemokines," *Immunopharmacol* 49:295-306, 2000.

Liang et al., "Suppression of inducible cyclooxygenase and nitric oxide synthase through activation of peroxisome proliferator-activated receptor-γ by flavonoids in mouse macrophages," *FEBS Lett* 496:12-18, May 4, 2001.

Millikan, "The Rationale for Using a Topical Retinoid for Inflammatory Acne," *Am J Clin Dermatol* 4(2):75-80, 2003.

Moroney et al., "Selectivity of Neutrophil 5-Lipoxygenase and Cyclo-oxygenase Inhibition by an Anti-inflammatory Flavonoid Glycoside and Related Aglycone Flavonoids," *Journal Pharm Pharmacol* 40:787-792, 1988.

Tordera et al., "Influence of Anti-Inflammatory Flavonoids on Degranulation and Arachidonic Acid Release in Rat Neutrophils," *Z Naturforsch* 49c:235-240, 1994.

Wakabayashi et al., "Wogonin inhibits inducible prostaglandin $E_2$ production in macrophages," *Eur J Pharmacol* 406:477-481, 2000.

You et al., "Inhibition of Cyclooxygenase/Lipoxygenase from Human Platelets by Polyhydroxylated/Methoxylated Flavonoids Isolated from Medicinal Plants," *Archives of Pharmaceutical Research* 22(1):18-24, Feb. 1999.

Zhang et al, "Inhibition of Cancer Cell Proliferation and Prostaglandin $E_2$ Synthesis by *Scutellaria Baicalensis*," *Cancer Research* 63:4037-4043, Jul. 15, 2003.

\* cited by examiner

COMPOSITION FOR TREATING ATOPIC DERMATITIS COMPRISING EXTRACTS OF BAMBOO AND *SCUTELLARIA*

CROSS-REFERENCE TO RELATED APPLICATIONS

This application is a continuation of U.S. application Ser. No. 12/445,159, filed Apr. 28, 2009 (now U.S. Pat. No. 8,247,007); which is a U.S. National Phase Application of International Application No. PCT/KR2007/005004, filed Oct. 12, 2007; which claims priority to Korea Application No. 10-2006-0099182, filed Oct. 12, 2006. These applications are incorporated herein by reference in their entirety.

TECHNICAL FIELD

The present invention is a composition comprising of a plant extract as an active ingredient for treating atopic dermatitis, specifically a mixture composition comprising of Bamboo extracts and *Scutellaria* extracts.

BACKGROUND ART

Atopic dermatitis is an allergic disease caused by a defect of a stratum corneum which is a protective wall located in the outermost part of the skin which is caused by hereditary, environmental, or immunological factors and is exacerbated in arid climates. Many people are afflicted by the atopic dermatitis, specifically 0.5-1% of the total population. In cases of minors, 5-10% of children are afflicted by the atopic dermatitis. 50% of patients can recover by their second birthday, and 25% can recover by puberty. However, 25% never recover and continue to suffer from atopic dermatitis into adulthood.

The main symptoms of atopic dermatitis are severe pruritus, xeroderma, eruption or oozing of the skin, boils, scale like skin (scaly skin), etc.

The pathogenesis of atopic dermatitis is not completely understood, but genetic factors are attributed to most cases of atopic dermatitis, and the pathogenesis is related to immune response. It has been shown that atopic dermatitis can be caused by a combination of dry skin, skin that is prone to itching more than the average person, infections caused by bacteria virus fungi, etc., and emotional and environmental factors.

Specifically, an antibody (IgE) produced by a mast cell during the body's process of naturally eliminating a material which causes a rash to form when in contact or invading the body causes a hypersensitive reaction when this same material invades the body again producing a histamine which causes the atopic dermatitis. The mast cell is distributed widely throughout organs such as, the skin, respiratory organs, mucosa of the gastrointestinal tract, circum of lymphatic duct, brain, and is known as the cell that causes diverse inflammation and allergic reactions. The histamine released from the mast cell causes inflammation and immediate allergic reaction by inducing vasodilation, smooth muscle-contraction of the gastrointestinal and/or bronchial tract, secretion of glandular cells, exacerbation of the reactions, etc., and serves as an intermediary for diverse biological effects such as secretion of mucus and local protein.

Pharmacotherapies, such as steroids, anti-histamines, antibiotics are usually prescribed for atopic dermatitis. The steroid agent (adrenal cortical hormone agent) can act as an anti-inflammatory and immuno-suppressant and has positive effect in treating the disease, but if used over a long period of time, side effects such as skin-weakening, symptom of systemic hormone, toxicity can result. Currently, uses of immune-suppression agents and novel anti-histamine agents have been studied for treating atopic dermatitis. However, anti-histamine agents cannot completely suppress the allergic reaction since other chemical transmitters in addition to the histamine can induce the allergic reaction. The mast cell releases other chemical transmitters such as leukotriene C4 and leukotriene B4 in addition to the histamine. Leukotriene C4 contracts the smooth muscle of bronchus like the histamine, and leukotriene B4 causes chronic inflammation by inducing neutrophil and eosinophil and injures neighboring cells.

Thus, a novel composition for the effective treatment of atopic dermatitis without the side-effects is required.

Bamboo belongs to the Poaceae family. There are about 280 known species of bamboo all over the world, and about 70 species grow naturally or are cultivated in Korea. There are 11 representative kinds of Bamboo; *Phyllostachys nigra*, *Phyllostachys bambusoides* (*Cedrela sinesis*), *Phyllostachys edulis* (*Phyllostachys puhescen*), *Phyllostachys nigra* for. *Punctata*, *Sasa borealis* var. *gracilis*, *Arundinaria simonii*, *Sasa borealis* var. *chiisanensis*, *Sasa borealis*, *Sasa albo-marginata*, *Pseudosasa japonica*, etc. Among them, *Phyllostachys bainbusoides* (*Cedrela sinesis*), *Phyllostachys nigra* and *Phyllostachys edulis* are cultivated. According to Dongeui-Bogam, Compendium of Materia Medica and the divine Farmer's Materia Medica, Bamboo is effective in treating palsy and hypertension, and was used to treat pneumonia and bronchitis to bring down fever, loosen phlegm and as a coolant. Recently, it has been reported that Bamboo has been used to treat hypertension, atherosclerosis and cardiovascular disease. Bamboo is also known to have anti-oxidant effect which is effective in the prevention of cancer and aging. Also, phytochemicals such as organic acid, dietary fiber, tannin, benzofuran within the plant are expected to contribute to preventing diseases of the circulatory system.

The conventional studies for bioactive compounds focusing on antimicrobial activity have been reported mostly in Korean and Japan. Japanese researchers discovered the 2,6-dimethylbenzoquinone and benzoic acid which are antimicrobial compounds in the leaf of Bamboo, and Korean Patent No. 10-0465113 discloses the effects of bamboo extract in improving blood circulation and preventing inflammation. Japanese Patent Publication H09-278662 discloses fats and oils which have anti-allergic effect contains the Bamboo extract obtained by using the soxhlet method using ether as a solvent, and WO 2002/07745 discloses that Bamboo extract obtained by using water has antipruritic effect which is effective in the treatment of atopic dermatitis.

*Scutellaria* has bioactive and pharmacological properties and has been used in oriental medicine for treating fevers and allergies. It acts by dilating blood vessels and brings down blood pressure, and inhibits atherosclerosis. Bicalin contained in *Scutellaria* is a kind of flavonoid which is effective to sedate or stop bleeding by suppressing the permeability of capillaries. Also, bicalin inhibits the release of chemical transmitters by strengthening the mast cell membrane and so can do anti-allergic action. Specifically, it is known that the pharmacological properties of *Scutellaria* are improving infections caused by allergies, inhibiting increased vascular permeability and alleviating inflammatory discharge of blood and congestion by strong anti-inflammatory effect, and these pharmacological properties are derived from bicalin. Bicalin is hydrolyzed to baicalein and glucuronic acid. Baicalein acts as a diuretic and glucuronic acid acts as deintoxicant. Korean Patent Publication No. 1996-0003725 discloses a therapeutic agent comprising of the flavonoid ingredient of *Scutellaria*. Korean Patent Publication No. 1996-0040370 discloses a composition for the prevention and treatment of alcohol disorder comprising of *Scutellaria* extract and flavone glycoside. Korean Patent Publication No. 2002-0031608 discloses a *Scutellaria* extract that has positive antimicrobial effect, and the process for preparing the extract and the pharmaceutical composition of the extract. Korean Patent No. 10-0522579 discloses a mixture extract of *Scutellaria* and Omija (Schizandra chinensia Baillon) which has anti-stress effect.

The above properties of Bamboo or *Scutellaria* have been known, but there has not been reported any therapeutic effect for atopic dermatitis using the mixture composition comprising of Bamboo extract and *Scutellaria* extract.

The inventors of the present invention have studied a novel compound for the treatment of atopic dermatitis. As a result, they discovered and confirmed that the mixture composition comprising Bamboo extract and *Scutellaria* extract can strongly inhibit the release of histamine and leukotrien without any side-effects and has positive therapeutic effect on atopic dermatitis, to complete the present invention.

DISCLOSURE OF THE INVENTION

The object of the present invention is to provide a composition comprising of a plant extract as an active ingredient which will have a positive therapeutic effect for the treatment and prevention of atopic dermatitis without any side-effects.

Also, the object of the present invention is to provide a use of mixture composition of Bamboo extract and *Scutellaria* extract for the manufacture of a medicament for the treatment and prevention of atopic dermatitis.

Also, the object of the present invention is to provide a method of the treatment and prevention of atopic dermatitis by administering to the subject a therapeutically effective amount of mixture composition of Bamboo extract and *Scutellaria* extract.

DETAILED DESCRIPTION OF THE INVENTION

Figure 1:
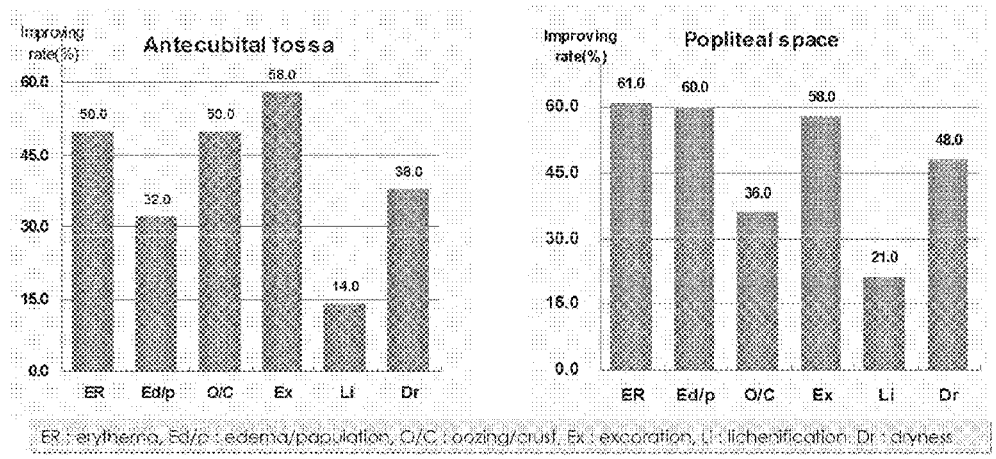
FIG. 1 is a graph showing the improvement rate of clinical trial items on antecubital space and popliteal space after administering the present extract.

To achieve the above objectives, the present invention provides a composition for the treatment of atopic dermatitis comprising of Bamboo extract and *Scutellaria* extract as an active ingredient.

Also, the present invention provides a use of mixture composition of Bamboo extract and *Scutellaria* extract for the manufacture of a medicament for the treatment and prevention of atopic dermatitis.

Also, the present invention provides a method of the treatment and prevention of atopic dermatitis by administering to the subject a therapeutically effective amount of mixture composition of Bamboo extract and *Scutellaria* extract.

In the composition of the present invention, Bamboo is selected from *Phyllostachys, Sasa* or *Pseudosasa*, and *Phyllostachys* is preferably selected from the group consisting of *Phyllostachys edulis, Phyllostachys nigra* var. *henonis, P. nigra, P. bainbusoides, P. pubescence, P. nigra* for. *punctata* and *P. comprossa*, and *Sasa* is preferably selected from the group consisting of *Sasa coreana Nakai, S. coreana, S. kurilensis, S. quelpaertensis, S. borealis, S. borealis* var. *chiisanensis* and *S. borealis* var. *gracilis*, and *Pseudosasa* is preferably selected from *Pseudosasa japonica* and *Pseudosasa japonica* var. *purpurascens*.

In the composition of the present invention, for Bamboo and *Scutellaria* commercially purchased herbs can be used. The whole herb, branch, shell, leaf, sprout, root, endodermis, etc., can be used, preferably in the form of powder or extract.

The Bamboo extract and *Scutellaria* extract of the present invention can be used by extracting Bamboo and *Scutellaria* with water, organic solvent, or mixing solvents thereof. Although all conventional solvents can be used as the above organic solvent, polar solvent such as water, $C_{1-4}$ alcohol (such as methanol, ethanol etc.), etc., or mixing solvent thereof is preferred. Preferably, water-insoluble fraction of 50-90% of ethanol extract or ethanol-soluble fraction of hot water extract can be used as the above bamboo extract.

The above extraction may be carried out by conventional methods such as hot water extraction, sonication, etc., and a lyophilized product of the extract can be used for the present composition. In addition, the extract can be further purified by conventional fractionation method or chromatography, and such fractionated material or purified material is also within the scope of the present invention.

In the composition of the present invention, Bamboo or *Scutellaria* can be used alone, but it is preferable to use a combined composition that Bamboo extract is additionally mixed with *Scutellaria* extract to show synergistic effect.

In the composition of the present invention, the synergistic effect at the time of administering the combination in comparison with administration of the extract alone was measured and confirmed by using the COLBY formula (COLBY S. R., Calculating synergistic and antagonistic response of herbicide combinations, Weeds 15, 20-22, 1967).

As shown above, when the composition is used in combination with Bamboo extract and *Scutellaria* extract, their weight ratios of Bamboo:*Scutellaria* could be in 1~10:1~10, but preferably 1~5:1~5, or more preferably 1~3:1~3.

The composition of the present invention can be prepared into conventional pharmaceutical preparations according to conventional methods in the pharmaceutical field, for example, solution such as drinks, syrup, capsule, granule, tablet, powder, pill, ointment, and emulsion, skin external preparation such as gel, etc., by mixing it with a pharmaceutically acceptable carrier, excipient, etc.; and can be administered orally or parenterally.

The composition of the present invention is appropriately administered depending on the extent of absorption of the active ingredients into the body; excretion rate; age, weight, sex, and condition of patient; severity of treated disease, etc. However, generally, the dosage for an adult is in solution 0.0001~100 mg/kg, or preferably 0.001~100 mg/kg, per day. It can be administered once a day or several times a day. The amount should not limit the scope of the present invention in any manner.

Hereinafter, the present invention will be described in more detail with reference to the following examples, but the scope of the present invention should not be construed to be limited thereby in any manner.

EXAMPLES

Example 1

Preparation of Bamboo Extract

Example 1-1

Preparation of Bamboo Ethanol Extract

Dried bamboo (20 kg) was extracted by adding 25% of ethanol (200 l) and heating the mixture at 80° C. for 6 hr. The extract was filtered and concentrated to remove the ethanol until the extract volume reached 5 l. The concentrated extract was then cooled to room temperature. The pellets were collected and dried to obtain the bamboo extract (390 g).

Example 1-2

Preparation of Bamboo Hot Water Extract

Dried bamboo (20 kg) was extracted by adding water in the amount equivalent to 10 times the weight of the dried bamboo and heating the mixture at 100° C. for 4 hr. The extract was filtered and concentrated under reduced pressure. The concentrated extract was added to ethanol (10 l) and stirred at 70° C. for 2 hr, and then cooled to room temperature. The pellets were filtered and concentrated under reduced pressure to obtain the bamboo extract (350 g).

Example 2

Preparation of *Scutellaria* Extract

*Scutellaria* (1 Kg) was added to water (8 l) and extracted by refluxing at 80° C. for 2 hr. The extract was cooled, filtered and concentrated, to obtain the *Scutellaria* extract powder (330 g).

Example 3

Preparation of Mixture Composition

The mixture composition was prepared by mixing Bamboo extract obtained from Example 1 and *Scutellaria* extract obtained from Example 2. The weight proportion of the Bamboo extract to the *Scutellaria* extract should be 1:1, 1:2, 1:3 or 2:1, 3:1.

EXPERIMENTS

Experiment 1

Measurement of Inhibition Activity of Releasing Histamine and Leukotrien from the Mast Cell According to the Examples The release of histamine and leukotrien from the mast cell is one of the major causes for the allergic reaction. The effect of the mixture composition of the Bamboo extract and the *Scutellaria* extract in inhibiting the release of histamine and leukotrien from the mast cell was measured.

Experiment 1-1

Isolation of the Mast Cell from Liver

Lung tissue (3 g/1 pig) was isolated from eight female guinea pigs (200 g) and fat tissue, bronchus and blood were removed from the lung tissue. The isolated lung tissue was treated with enzyme (5 mg/ml of collagenase, 1.8 unit/27 μl of elastase) by using Tyrode TGCM buffer containing $Ca^{2+}$, $Mg^{2+}$ and 0.1% of gelatin at 3 times for 15, 15, 25 mins. The each enzyme treated lung tissue was filtered by nylon mesh and metal mesh (100 μm), and then centrifuged (called 'monodispersed mast cell'). The pellets was suspended with TG buffer (16 ml) containing 0.1% of gelatin, but no $Ca^{2+}$ and $Mg^{2+}$, and centrifuged by loading to rough Percoll (1.041 mg/ml density) at 1,400 rpm for 25 mins, to obtain the pellets. The pellets were re-suspended with TG buffer (8 ml) and centrifuged by loading to discontinuous Percoll (1.06-1.10 mg/ml density) at 1,400 rpm for 25 mins, to isolate several cell layers. Among the several cell layers, the third and fourth layers were washed twice with TGCM buffer since the mast cell exists in third and fourth layers. The whole cell and mast cell were stained with trypan blue and alcian blue. The purity of the mast cell was measured by calculating the number of cells, to obtain about 80-90% of the mast cell.

Experiment 1-2

Inhibition of Releasing Histamine from the Mast Cell

The mast cell (4105 cells) was treated with guinea pig IgG1 antibody (anti-OVA 1 ml/106 cells) at 37° C. for 45 mins, and washed with TGCM buffer to remove anti-OVA antibodies which are not bound to the membrane of the mast cell. The mast cell was suspended with TGCM buffer (1 ml) and pre-treated with each reagents (30 μg concentration). The mast cell was reacted by sensitizing using ovalbumin (1.0 μg/μl) for 10 mins, cooled in ice, and centrifuged, to measure histamine from the supernant.

The amount of histamine in each sample was measured by modifying the method of Siraganian and using automated continuous-flow extraction and a flourometic analyzer (Astoria analyzer series 300, Astoria-pacific international, Oregon, USA). 1N-hydrochloric acid, 0.73M phosphoric acid, 5N sodium hydroxide, 1N sodium hydroxide, saline diluents and sampler wash, o-phthaladehyde solution was prepared and connected to a tube linked to the analyzer. The storage solution of histamine was diluted to 20 ng, 10 ng, 5 ng, 3 ng and 1 ng, and the concentration-dependent result of standard curve was obtained. Then, each sample was diluted with 2% of perchloric acid and the amount of histamine was measured. The result showed that the Bamboo extract and the *Scutellaria* extract showed inhibition activity, respectively, and the mixture composition of the Bamboo extract and the *Scutellaria* extract also showed high inhibition activity. The synergistic effect at the time of administering the combination in comparison with administration of the extract alone was measured and confirmed by using the COLBY formula (COLBY S. R., Calculating synergistic and antagonistic response of herbicide combinations, Weeds 15, 20-22, 1967) (Table 1).

TABLE 1

The inhibition activity of releasing histamine
from the mast cell per each extract.

| Sample | Inhibition activity (%) |
|---|---|
| Control | 32.5 ± 0.25 |
| Bamboo extract | 22.4 ± 0.09 (31.1%) |
| *Scutellaria* extract | 26.4 ± 0.11 (18.8%) |
| Mixture composition (Bamboo:*Scutellaria* = 1:1) | 10.1 ± 0.25 (70.5%) |
| Mixture composition (Bamboo:*Scutellaria* = 1:2) | 15.4 ± 0.46 (52.6%) |
| Mixture composition (Bamboo:*Scutellaria* = 1:3) | 19.7 ± 0.52 (39.4%) |
| Mixture composition (Bamboo:*Scutellaria* = 2:1) | 9.3 ± 0.32 (71.3%) |
| Mixture composition (Bamboo:*Scutellaria* = 3:1) | 13.2 ± 0.11 (59.4%) |

Experiment 1-3

Inhibition of Releasing Leukotrien from the Mast Cell

The amount of leukotrien in each sample was measured by using the method of Aharoney et al. (Biochem. Biophys. Res. Commun., p 574-579, 1983). The leukotrien antibody was suspended with 5 mM MES buffer containing 0.1% of gelatin, and to each tube the supernant of the cell (100 µl) which was treated with a reagent (30 µg) was added. The leukotrien antibody and [$^3$H] leukotrien D4 (LTD$_4$) were added to the supernant and was allowed to react at 4° C. for 2 hr. The reaction was stopped by using dextran coated charcoal and the inhibition activity was measured by using liquid scintillation spectrometry. The results showed that the Bamboo extract and the *Scutellaria* extract showed inhibition activity, respectively, and the mixture composition of the Bamboo extract and the *Scutellaria* extract also showed high inhibition activity. The synergistic effect at the time of administering the combination in comparison with administration of the extract alone was measured and confirmed by using the COLBY formula (COLBY S. R., Calculating synergistic and antagonistic response of herbicide combinations, Weeds 15, 20-22, 1967) (Table 2).

TABLE 2

The inhibition activity of releasing leukotrien
from the mast cell per each extract.

| Sample | Inhibition activity (%) |
|---|---|
| Control | 679.0 ± 54.19 |
| Bamboo extract | 449.0 ± 40.47 (33.8%) |
| *Scutellaria* extract | 569.4 ± 32.89 (16.1%) |
| Mixture composition (Bamboo:*Scutellaria* = 1:1) | 149.5 ± 8.26 (78.0%) |
| Mixture composition (Bamboo:*Scutellaria* = 1:2) | 282.1 ± 47.55 (58.5%) |
| Mixture composition (Bamboo:*Scutellaria* = 1:3) | 350.1 ± 33.1 (48.4%) |
| Mixture composition (Bamboo:*Scutellaria* = 2:1) | 147.5 ± 11.92 (78.3%) |
| Mixture composition (Bamboo:*Scutellaria* = 3:1) | 322.9 ± 33.65 (52.4%) |

Experiment 2

Clinical Trials 20 patients suffering from severe atopic dermatitis were tested by using the mixture composition of Bamboo extract and *Scutellaria* extract selected from Experiment 1 for 4 weeks. The present composition was spread onto the popliteal fossa and the antecubital fossa, and the results were investigated.

In the clinical trial, the effects before and after using the product were estimated by using the Local SCORAD index. The results were estimated by rating the degrees of 6 intensity items, erythema, edem/population, oozing/crusting, excoriation, lichenification, dryness on a scale of 4 (0=absent, 1=mild, 2=moderate, 3=severe) for the right and left side of popliteal fossa and antecubital fossa which were then used to show improvement rate.

Figure 2:
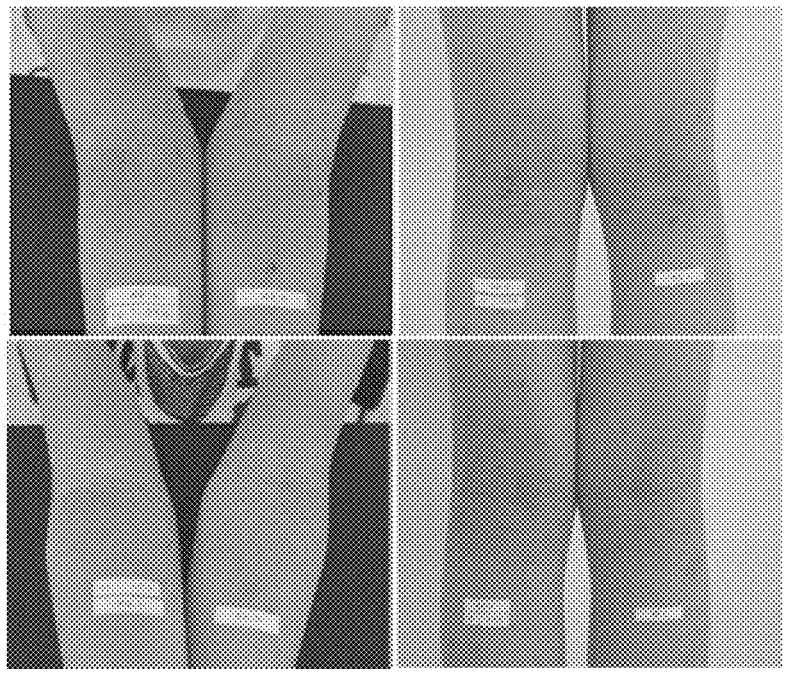
FIG. 2 is a digital steel photo showing the improvement effect of atopic dermatitis according to administration of the present extract by comparing photos taken before and after using the product.
Figure 3:
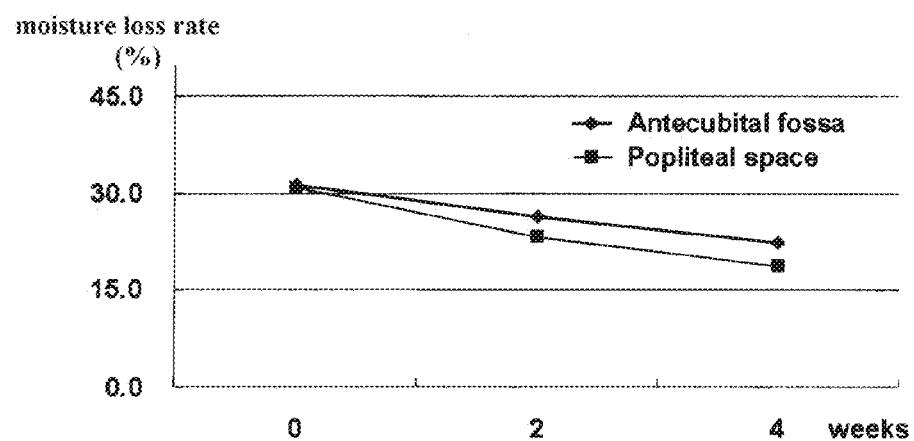
FIG. 3 is a graph showing measurement result of the moisture loss rate ($g/m^2h$) which occurred per unit area and per unit time by using Tewameter TM300 (Courage+Khazaka, Germany) on 10 cm lower part of popliteal fossa and antecubital fossa at the time before the product was used and after the product was used.

The results showed that there was improvement effect after using the product, specifically there was more than 50% improvement in erythema, oozing/crusting and excoriation (FIG. 1). The result was photographed by using a Digital Still Camera (DSC-S75, Sony) at the time before the product was used and after the product was used (FIG. 2). Also, the moisture loss (g/m$^2$·h) due to evaporation which occurred per unit area and per unit time was estimated by using Tewameter TM300 (Courage+Khazaka, Germany) on 10 cm lower part of popliteal fossa and antecubital fossa at the time before the product was used and after the product was used. The moisture loss on trandermal was reduced each time, specifically the improvement on the antecubital fossa was better than on the popliteal fossa (FIG. 3).

Industrial Applicability

The present invention is a natural ingredient obtained from a plant, and can control immune responses by inhibiting the release of histamine and leukotrien. It has been confirmed that the present invention is safe and is beneficial to the treatment of atopic dermatitis, and thus, the composition can be used for the treatment and prevention of atopic dermatitis.

The invention claimed is:

1. A method for treating allergic skin disease, comprising administering to a subject a therapeutically effective amount of a composition comprising a Bamboo extract and a *Scutellaria* extract, wherein the weight ratio of Bamboo extract to *Scutellaria* extract ranges from 1:3 to 3:1.

2. The method according to claim 1, wherein the Bamboo extract is a water-insoluble fraction of a 50-90% ethanol extract.

3. The method according to claim 2, wherein the *Scutellaria* extract is obtained by extraction with water, methanol, ethanol or a mixture thereof.

4. The method according to claim 1, wherein the Bamboo extract is an ethanol-soluble fraction of a hot water extract.

5. The method according to claim 4, wherein the *Scutellaria* extract is obtained by extraction with water, methanol, ethanol or a mixture thereof.

6. The method according to claim 1, wherein the composition inhibits a release of histamine, leukotriene, or a combination thereof.

7. The method according to claim 1, wherein the method comprises treating atopic dermatitis.

8. The method according to claim 1, wherein the method comprises treating erythema, edema, papulation, oozing, crust, excoriation, lichenification or dryness.

9. The method according to claim 1, wherein the method decreases transdermal moisture loss.

10. The method according to claim 1, wherein the composition is formulated with a pharmaceutically acceptable carrier or excipient.

11. The method according to claim 1, wherein the composition is administered topically.

12. The method according to claim 1, wherein the composition is prepared as a gel, ointment, or emulsion.

13. The method according to claim 12, wherein the composition is administered topically.

* * * * *